United States Patent
Hasegawa et al.

(10) Patent No.: US 10,991,981 B2
(45) Date of Patent: Apr. 27, 2021

(54) NONAQUEOUS ELECTROLYTE SECONDARY BATTERY

(71) Applicant: Panasonic Intellectual Property Management Co., Ltd., Osaka (JP)

(72) Inventors: Masaki Hasegawa, Osaka (JP); Yuanlong Zhong, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 124 days.

(21) Appl. No.: 16/472,561

(22) PCT Filed: Dec. 14, 2017

(86) PCT No.: PCT/JP2017/044812
§ 371 (c)(1),
(2) Date: Jun. 21, 2019

(87) PCT Pub. No.: WO2018/116941
PCT Pub. Date: Jun. 28, 2018

(65) Prior Publication Data
US 2019/0326640 A1    Oct. 24, 2019

(30) Foreign Application Priority Data

Dec. 22, 2016  (JP) .............................. JP2016-250044

(51) Int. Cl.
*H01M 10/0567* (2010.01)
*C07D 251/34* (2006.01)
*C07D 319/12* (2006.01)
*H01M 4/525* (2010.01)
*H01M 10/0525* (2010.01)
*H01M 10/0569* (2010.01)
*H01M 4/02* (2006.01)

(52) U.S. Cl.
CPC ...... *H01M 10/0567* (2013.01); *C07D 251/34* (2013.01); *C07D 319/12* (2013.01); *H01M 4/525* (2013.01); *H01M 10/0525* (2013.01); *H01M 10/0569* (2013.01); *H01M 2004/028* (2013.01); *H01M 2300/0025* (2013.01)

(58) Field of Classification Search
CPC .......... H01M 10/0567; H01M 10/0569; C17D 251/34
See application file for complete search history.

(56) References Cited

U.S. PATENT DOCUMENTS

| | | | |
|---|---|---|---|
| 2006/0228625 A1 | 10/2006 | Kawashima | |
| 2006/0276644 A1* | 12/2006 | Childress | C07F 7/1892 544/193 |
| 2012/0088160 A1* | 4/2012 | Zhang | H01G 11/30 429/328 |
| 2014/0186721 A1* | 7/2014 | Zhang | H01M 10/0567 429/331 |
| 2014/0302402 A1* | 10/2014 | Chen | H01M 10/0569 429/333 |
| 2015/0050564 A1 | 2/2015 | Mizuno et al. | |
| 2015/0364794 A1 | 12/2015 | Nakazawa et al. | |
| 2016/0211553 A1 | 7/2016 | Ito et al. | |
| 2020/0373574 A1* | 11/2020 | Kokubu | H01M 4/623 |

FOREIGN PATENT DOCUMENTS

| | | |
|---|---|---|
| JP | 2006-294373 A | 10/2006 |
| JP | 2013-182807 A | 9/2013 |
| JP | 2014-41820 A | 3/2014 |
| JP | 2014-194930 A | 10/2014 |
| WO | 2015/046475 A1 | 4/2015 |

* cited by examiner

*Primary Examiner* — Matthew J Merkling
(74) *Attorney, Agent, or Firm* — Westerman, Hattori, Daniels & Adrian, LLP

(57) ABSTRACT

This nonaqueous electrolyte secondary battery is provided with a positive electrode, a negative electrode and a non-aqueous electrolyte. The non-aqueous electrolyte contains: a non-aqueous solvent that contains a fluorine-containing cyclic carbonate; an isocyanuric acid derivative such as triallyl isocyanurate; and a cyclic carboxylic acid anhydride such as diglycolic acid anhydride.

6 Claims, No Drawings

NONAQUEOUS ELECTROLYTE SECONDARY BATTERY

TECHNICAL FIELD

The present invention relates to a technique of a non-aqueous electrolyte secondary battery.

BACKGROUND ART

For example, Patent Literature 1 discloses a non-aqueous electrolyte secondary battery including a positive electrode, a negative electrode, and an electrolyte including a fluorine-containing cyclic carbonate. Patent Literature 1 also discloses that cyclic characteristics at room temperature can be improved by using the electrolyte including a fluorine-containing cyclic carbonate.

For example, Patent Literature 2 discloses that when an isocyanate compound such as triallyl isocyanurate is added to an electrolyte including a fluorine-containing cyclic carbonate, an improving effect on the battery properties is provided.

For example, Patent Literature 3 also discloses that an isocyanate compound is added to an electrolyte including a fluorine-containing cyclic carbonate.

CITATION LIST

Patent Literature

PATENT LITERATURE 1: Japanese Unexamined Patent Application Publication No. 2013-182807
PATENT LITERATURE 2: Japanese Unexamined Patent Application Publication No. 2014-194930
PATENT LITERATURE 3: Japanese Unexamined Patent Application Publication No. 2014-41820

SUMMARY

However, a non-aqueous electrolyte secondary battery including an electrolyte including a fluorine-containing cyclic carbonate and an isocyanate compound does not exhibit the sufficient effect of preventing the decrease in the capacity due to charging/discharging cycles in an environment at a high temperature. Particularly, a non-aqueous electrolyte secondary battery including such an electrolyte in a combination with a positive electrode active material including a Ni-containing lithium composite oxide as a main component hardly exhibits the effect of preventing the decrease in the capacity due to charging/discharging cycles in an environment at a high temperature.

Therefore, it is an advantage of the present disclosure to provide a non-aqueous electrolyte secondary battery that can prevent the decrease in the capacity due to charging/discharging cycles in an environment at a high temperature even when using a positive electrode active material including a Ni-containing lithium composite oxide as a main component.

The non-aqueous electrolyte secondary battery according to one aspect of the present disclosure comprises: a positive electrode that comprises a positive electrode active material comprising a Ni-containing lithium composite oxide as a main component; a negative electrode; and a non-aqueous electrolyte, wherein the non-aqueous electrolyte comprises: a non-aqueous solvent comprising a fluorine-containing cyclic carbonate; an isocyanuric acid derivative; and a cyclic carboxylic anhydride.

The isocyanuric acid derivative is represented by the formula below:

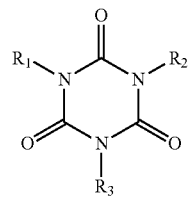

[Formula 1]

wherein $R_1$ to $R_3$ are each independently $-C_nH_{2n}-CH=CH_2$ or hydrogen, provided that at least one of $R_1$ to $R_3$ is $-C_nH_{2n}-CH=CH_2$; and n is an integer.

The cyclic carboxylic anhydride is represented by the formula below:

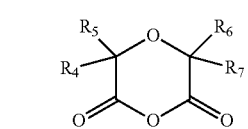

[Formula 2]

wherein $R_4$ to $R_7$ are each independently hydrogen, an alkyl group, an alkene group, or an aryl group.

The non-aqueous electrolyte secondary battery according to one aspect of the present disclosure can prevent the decrease in the capacity due to charging/discharging cycles in an environment at a high temperature though it uses a positive electrode active material including a Ni-containing lithium composite oxide as a main component.

DESCRIPTION OF EMBODIMENTS (Function of Non-Aqueous Electrolyte in Present Disclosure)

In a non-aqueous electrolyte including a fluorine-containing cyclic carbonate, a part of the fluorine-containing cyclic carbonate is decomposed on the surface of the negative electrode in initial charge to form a film (SEI film) on the surface of the negative electrode. Generally, the formation of the SEI film derived from the fluorine-containing cyclic carbonate prevents the decomposition of the non-aqueous electrolyte during subsequent charging/discharging processes. However, the SEI film derived from the fluorine-containing cyclic carbonate has poor heat-stability, and the SEI film is therefore broken in an environment at a high temperature. As a result, the decomposition of the components of the non-aqueous electrolyte that occur in the charging/discharging processes proceeds, and a product of the side reaction, which inhibits the electrode reaction, thus deposits on the negative electrode. Therefore, the decrease in the capacity occurs due to charging/discharging cycles in an environment at a high temperature.

It is considered that the decrease in the capacity due to charging/discharging cycles in an environment at a high temperature can be prevented by coexistence of an isocyanuric acid derivative, which is conventionally known to improve the battery performance. However, such a preventing effect still cannot be obtained when using a positive electrode active material including a Ni-containing lithium composite oxide as a main component. The reason for this is probably as follows: a side reaction between Ni and the non-aqueous electrolyte including the isocyanuric acid derivative occurs on the surface of the positive electrode active material to thereby produce a soluble reaction product, which moves toward to the negative electrode and deteriorates the film on the surface of the negative electrode.

The inventors have found that the decrease in the capacity due to charging/discharging cycles in an environment at a high temperature can be prevented by additional coexistence of a cyclic carboxylic anhydride. The reason for this is probably because the cyclic carboxylic anhydride and the isocyanuric acid derivative together form on the surface of the negative electrode a film having a resistance to the soluble reaction product produced by the side reaction due to Ni. Furthermore, it is considered that the film exhibits a small inhibitory effect on the electrode reaction, and it has also been found that the film exhibits the additional effect of improving the initial capacity of the non-aqueous secondary battery. Both effects, specifically, the improvement in the initial capacity and the prevention of the decrease in the capacity due to charging/discharging cycles in an environment at a high temperature are exhibited only when both the isocyanuric acid derivative and the cyclic carboxylic anhydride coexist.

An exemplary non-aqueous electrolyte secondary battery according to the present embodiment will now be described below.

The exemplary non-aqueous electrolyte secondary battery according to the present embodiment includes a positive electrode, a negative electrode, and a non-aqueous electrolyte. A separator is preferably provided between the positive electrode and the negative electrode. Specifically, the non-aqueous electrolyte secondary battery has a structure in which an electrode assembly and the non-aqueous electrolyte are housed in an exterior body, the electrode assembly having a wound structure in which the positive electrode and the negative electrode are wound together with the separator interposed therebetween. An electrode assembly in another form may be used instead of the electrode assembly having a wound structure, including an electrode assembly having a laminated structure in which positive electrodes and negative electrodes are laminated with separators interposed therebetween. The form of the non-aqueous electrolyte secondary battery is not particularly limited, and examples thereof include a cylindrical shape, a rectangular shape, a coin shape, a button shape, and a laminate.

[Non-Aqueous Electrolyte]

The non-aqueous electrolyte includes: a non-aqueous solvent including a fluorine-containing cyclic carbonate; an isocyanuric acid derivative; a cyclic carboxylic anhydride; and an electrolyte salt. The non-aqueous electrolyte is not limited to a liquid electrolyte (non-aqueous electrolyte solution), and may be a solid electrolyte using a polymer gel or the like.

The fluorine-containing cyclic carbonate included in the non-aqueous solvent is not particularly limited as long as it is a cyclic carbonate containing at least one fluorine atom. Examples thereof include monofluoroethylene carbonate (FEC), 1,2-difluoroethylene carbonate, 1,2,3-trifluoropropylene carbonate, 2,3-difluoro-2,3-butylene carbonate, and 1,1,1,4,4,4-hexafluoro-2,3-butylene carbonate. Among these, FEC is preferable in view of, for example, reducing the amount of hydrofluoric acid generated at a high temperature.

The content of the fluorine-containing cyclic carbonate is preferably, for example, 0.1 vol % or more and 30 vol % or less, more preferably 10 vol % or more and 20 vol % or less, based on the total volume of the non-aqueous solvent. If the content of the fluorine-containing cyclic carbonate is less than 0.1 vol %, the amount of the SEI film to be produced that is derived from the fluorine-containing cyclic carbonate may be small to thereby decrease cyclic characteristics at room temperature. If the content of the fluorine-containing cyclic carbonate is more than 30 vol %, the amount of the SEI film to be produced that is derived from the fluorine-containing cyclic carbonate may be so large that the effect of the isocyanuric acid derivative and the cyclic carboxylic anhydride added may not be exhibited sufficiently.

In addition to the fluorine-containing cyclic carbonate, the non-aqueous solvent may include a fluorine-free solvent, for example. Examples of the fluorine-free solvent include cyclic carbonate esters, chain carbonate esters, carboxylate esters, cyclic ethers, linear ethers, nitriles such as acetonitrile, amides such as dimethylformamide, and mixed solvents thereof.

Examples of the cyclic carbonate esters include ethylene carbonate (EC), propylene carbonate (PC), and butylene carbonate. Examples of the chain carbonate esters include dimethyl carbonate, ethyl methyl carbonate (EMC), diethyl carbonate, methyl propyl carbonate, ethyl propyl carbonate, and methyl isopropyl carbonate.

Examples of the carboxylate esters include methyl acetate, ethyl acetate, propyl acetate, methyl propionate (MP), ethyl propionate, and γ-butyrolactone.

Examples of the cyclic ethers include 1,3-dioxolane, 4-methyl-1,3-dioxolane, tetrahydrofuran, 2-methyltetrahydrofuran, propylene oxide, 1,2-butylene oxide, 1,3-dioxane, 1,4-dioxane, 1,3,5-trioxane, furan, 2-methylfuran, 1,8-cineole, and crown ethers.

Examples of the chain ethers include 1,2-dimethoxyethane, diethyl ether, dipropyl ether, diisopropyl ether, dibutyl ether, dihexyl ether, ethyl vinyl ether, butyl vinyl ether, methyl phenyl ether, ethyl phenyl ether, butyl phenyl ether, pentyl phenyl ether, methoxytoluene, benzyl ethyl ether, diphenyl ether, dibenzyl ether, o-dimethoxybenzene, 1,2-diethoxyethane, 1,2-dibutoxyethane, diethylene glycol dimethyl ether, diethylene glycol diethyl ether, diethylene glycol dibutyl ether, 1,1-dimethoxymethane, 1,1-diethoxyethane, triethylene glycol dimethyl ether, and tetraethylene glycol dimethyl ether.

The isocyanuric acid derivative included in the non-aqueous electrolyte is represented by the formula below:

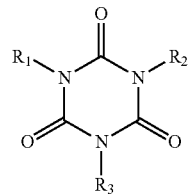

[Formula 3]

wherein $R_1$ to $R_3$ are each independently —$C_nH_{2n}$—CH=$CH_2$ or hydrogen, provided that at least one of $R_1$ to $R_3$ is —$C_nH_{2n}$—CH=$CH_2$; and n is an integer, preferably 1 to 20, for example. It is considered that a strong film is formed from an isocyanuric acid and the cyclic carboxylic anhydride on the negative electrode. Furthermore, it can be inferred that the film is polymerized due to the presence of the double bond in $R_1$ to $R_3$ and that a stronger film is thus formed.

Specific examples of the isocyanuric acid derivative included in the non-aqueous electrolyte include diallyl isocyanurate, triallyl isocyanurate, tributenyl isocyanurate, tripentenyl isocyanurate, and trihexenyl isocyanurate. Among these, triallyl isocyanurate is preferable in view of the both effects of improving the initial capacity and preventing the decrease in the capacity due to charging/discharging cycles in an environment at a high temperature. Triallyl isocyanurate is represented by the structural formula below.

[Formula 4]

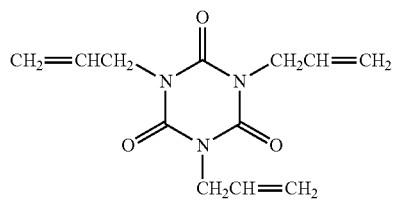

For example, the content of the isocyanuric acid derivative included in the non-aqueous electrolyte is preferably within the range of 0.1 mass % or more and 1.5 mass % or less, more preferably within the range of 0.25 mass % or more and 1 mass % or less, even more preferably within the range of 0.25 mass % or more and 0.5 mass % or less, based on the total mass of the non-aqueous electrolyte, in view of preventing the decrease in the capacity in an environment at a high temperature considered to be due to the side reaction on the positive electrode and so on. If the content is less than 0.1 mass %, the effect of preventing the decrease in the capacity due to charging/discharging cycles in an environment at a high temperature may be small. If the content is more than 1.5 mass %, the decrease in the capacity in an environment at a high temperature may be large.

The cyclic carboxylic anhydride included in the non-aqueous electrolyte is represented by the formula below:

[Formula 5]

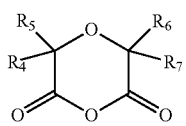

wherein $R_4$ to $R_7$ are each independently hydrogen, an alkyl group, an alkene group, or an aryl group.

Specific examples of the cyclic carboxylic anhydride included in the non-aqueous electrolyte include diglycolic anhydride, methyldiglycolic anhydride, dimethyldiglycolic anhydride, ethyldiglycolic anhydride, methoxydiglycolic anhydride, ethoxydiglycolic anhydride, vinyl diglycolic anhydride, allyl diglycolic anhydride, divinyl diglycolic anhydride, and divinyl diglycolic anhydride. Among these, diglycolic anhydride, in which all $R_4$ to $R_7$ are hydrogen, is preferable in view of the both effects of improving the initial capacity and preventing the decrease in the capacity due to charging/discharging cycles in an environment at a high temperature.

For example, the content of the cyclic carboxylic anhydride included in the non-aqueous electrolyte is preferably within the range of 0.1 mass % or more and 1.5 mass % or less, more preferably within the range of 0.25 mass % or more and 1 mass % or less, even more preferably within the range of 0.25 mass % or more and 0.75 mass % or less, based on the total mass of the non-aqueous electrolyte, in view of preventing the decrease in the capacity in an environment at a high temperature and so on. If the content is less than 0.1 mass %, the effect of preventing the decrease in the capacity due to charging/discharging cycles in an environment at a high temperature may be small. If the content is more than 1.5 mass %, the decrease in the capacity in an environment at a high temperature may be large.

The electrolyte salt included in the non-aqueous electrolyte is preferably a lithium salt. As the lithium salt, those generally used as a supporting electrolyte for conventional non-aqueous electrolyte secondary batteries can be used. Specific examples thereof include $LiPF_6$, $LiBF_4$, $LiAsF_6$, $LiClO_4$, $LiCF_3SO_3$, $LiN(FSO_2)_2$, $LiN(C_lF_{2l+1}SO_2)(C_mF_{2m+1}SO_2)$ (where l and m are each an integer of 0 or more), $LiC(C_pF_{2p+1}SO_2)(C_qF_{2q+1}SO_2)(C_rF_{2r+1}SO_2)$ (where p, q, and r are each an integer of 0 or more), $Li[B(C_2O_4)_2]$ (lithium bis(oxalate)borate (LiBOB)), $Li[B(C_2O_4)F_2]$, and $Li[P(C_2O_4)F_4]$, and $Li[P(C_2O_4)_2F_2]$. These lithium salts may be used singly or in combinations of two or more thereof.

[Positive Electrode]

The positive electrode includes, for example, a positive electrode collector such as metal foil and a positive electrode active material layer formed on the positive electrode collector. Foil of a metal, such as aluminum, that is stable in the electric potential range of the positive electrode, a film with such a metal disposed as an outer layer, and the like can be used for the positive electrode collector. The positive electrode can be produced by, for example, applying a positive electrode mixture slurry containing the positive electrode active material, the binder, and other components to the positive electrode collector, drying the resulting coating, and then rolling the resulting product to form the positive electrode active material layer on the positive electrode collector.

The positive electrode active material includes a Ni-containing lithium composite oxide as a main component. The main component herein means the component contained in the largest amount among materials constituting the positive electrode active material. In the positive electrode active material including a Ni-containing lithium composite oxide as a main component, a product of the side reaction due to nickel is likely to be produced, which leads to the decrease in the capacity due to charging/discharging cycles in an environment at a high temperature. However, when using an electrolyte in which an isocyanuric acid derivative and a cyclic carboxylic anhydride coexist as in the present embodiment, the decrease in the capacity due to charging/discharging cycles in an environment at a high temperature can be prevented, and the initial capacity can also be improved. For example, the content of the Ni-containing lithium composite oxide is preferably 50 mass % or more, more preferably 80 mass % or more, based on the total mass of the positive electrode active material.

The Ni-containing lithium composite oxide is not particularly limited, and for example, preferred is a lithium composite oxide having a nickel content of 20 mol % or more based on the total molar amount of the metal elements excluding nickel. When the nickel content is 20 mol % or more, a high battery capacity can be obtained, but a product of the side reaction due to nickel is more likely to be produced. However, by using an electrolyte in which an isocyanuric acid derivative and a cyclic carboxylic anhydride coexist as in the present embodiment, the decrease in the capacity due to charging/discharging cycles in an environment at a high temperature can be prevented while a high battery capacity can also be obtained.

For example, the Ni-containing lithium composite oxide is preferably a composite oxide represented by the general formula $Li_xNi_yM_{(1-y)}O_2$ (wherein 0.1≤x≤1.2, 0.2≤y≤1, M represents at least one metal element). Examples of the metal element M include Co, Mn, Mg, Zr, Al, Cr, V, Ce, Ti, Fe, K, Ga, and In. Among these, at least one of cobalt (Co), manganese (Mn), and aluminum (Al) is preferably contained. Particularly, Co and Al are preferably contained in view of, for example, capacity.

The positive electrode active material may include a Ni-free lithium composite oxide, such as a cobalt-containing lithium composite oxide or a manganese-containing lithium composite oxide, in addition to the Ni-containing lithium composite oxide. For example, the content of the Ni-free lithium composite oxide is preferably 50 mass % or less based on the total mass of the positive electrode active material.

As an electrical conductor, carbon powders such as carbon black, acetylene black, Ketjenblack, and graphite may be used singly or in combinations of two or more thereof.

Examples of the binder include a fluorinated polymer and a rubber polymer. Examples of the fluorinated polymer include polytetrafluoroethylene (PTFE), poly (vinylidene fluoride) (PVdF), and modified products thereof, and examples of the rubber polymer include an ethylene/propylene/isoprene copolymer and an ethylene/propylene/butadiene copolymer. These may be used singly or in combinations of two or more thereof.

[Negative Electrode]

The negative electrode includes, for example, a negative electrode collector such as a metal foil, and a negative electrode active material layer formed on the negative electrode collector. Foil of a metal, such as copper, that is stable in the electric potential range of the negative electrode, a film with such a metal disposed as an outer layer, and the like can be used for the negative electrode collector. The negative electrode active material layer preferably includes a thickener and a binder in addition to the negative electrode active material. The negative electrode can be produced by, for example, applying to the negative electrode collector a negative electrode mixture slurry containing the negative electrode active material, the thickener, and the binder dispersed in water in a given weight ratio, drying the resulting coating, and then rolling the resulting product to form a negative electrode active material layer on the negative electrode collector.

Examples of the negative electrode active material include a carbon material and a non-carbon material that can reversibly intercalate and deintercalate lithium ions. Examples of the carbon material include graphite, non-graphitizable carbon, graphitizable carbon, fibrous carbon, coke, and carbon black. Examples of the non-carbon material include silicon, tin, and an alloy and an oxide including silicon or tin mainly.

As the binder, PTFE, for example, can be used as in the positive electrode, and a styrene/butadiene copolymer (SBR) or a modified product thereof may also be used, for example. As the thickener, carboxymethylcellulose (CMC) can be used, for example.

[Separator]

An ion-permeable and insulating porous sheet is used as the separator, for example. Specific examples of the porous sheet include a microporous thin film, woven fabric, and nonwoven fabric. Suitable examples of the material for the separator include olefin resins such as polyethylene and polypropylene, and cellulose. The separator may be a laminate including a cellulose fiber layer and a layer of fibers of a thermoplastic resin such as an olefin resin. The separator may be a multi-layered separator including a polyethylene layer and a polypropylene layer, and a separator a surface of which is coated with a material such as an aramid resin or ceramic may also be used as the separator.

EXAMPLES

Hereinafter, the present disclosure will be further described by way of Examples, but is not limited to the following Examples.

Example 1

[Production of Positive Electrode]

A lithium composite oxide represented by the general formula: $LiNi_{0.8}Co_{0.15}Al_{0.05}O_2$ was used as a positive electrode active material. 100 mass % of the positive electrode active material, 1 mass % of acetylene black as an electrical conductor, and 0.9 mass % of polyvinylidene fluoride as a binder were mixed, and N-methyl-2-pyrrolidone (NMP) was added thereto to prepare a positive electrode mixture slurry. Then, the positive electrode mixture slurry was applied to both sides of a positive electrode collector made of aluminum having a thickness of 15 μm according to the doctor blade method, and the resulting coating was rolled to form a positive electrode active material layer having a thickness of 70 μm on each side of the positive electrode collector. The resulting product was used as a positive electrode.

[Production of Negative Electrode]

100 mass % of graphite as the negative electrode active material and 1 mass % of a styrene/butadiene copolymer (SBR) as a binder were mixed, and water was added thereto to prepare a negative electrode mixture slurry. Then, the negative electrode mixture slurry was applied to both sides of a negative electrode collector made of copper having a thickness of 10 μm according to the doctor blade method, and the resulting coating was rolled to form a negative electrode active material layer having a thickness of 100 μm on each side of the negative electrode collector. The resulting product was used as a negative electrode.

[Preparation of Electrolyte]

In a mixed solvent consisting of fluorinated ethylene carbonate (FEC), ethyl methyl carbonate (EMC), and dimethyl carbonate (DMC) mixed in a volume ratio (25° C.) of 15:45:40, $LiPF_6$ was dissolved at a concentration of 1.3 mol/L, and 0.75 mass % triallyl isocyanurate and 0.5 mass % of diglycolic anhydride were dissolved therein to prepare an electrolyte.

[Production of Cylindrical Battery]

The positive electrode and the negative electrode were each cut into a given size, followed by attaching an electrode tab to each electrode, and they were wound together with the separator therebetween to produce an electrode assembly of wound type. Then, the electrode assembly with dielectric plates disposed on its top and bottom was housed in an exterior can made of steel plated with Ni and having a diameter of 18 mm and a height of 65 mm. The tab for the negative electrode was welded to the inner bottom of the battery exterior can, and the tab for the positive electrode was welded to the bottom plate of a sealing member. The electrolyte above described was poured in the exterior can through the opening thereof, and the exterior can was hermetically closed with the sealing member to produce a cylindrical battery.

Example 2

An electrolyte was prepared in the same manner as in Example 1, except that when preparing the electrolyte, 0.5 mass % of triallyl isocyanurate and 0.25 mass % of diglycolic anhydride were dissolved to prepare the electrolyte. A cylindrical battery was produced using the electrolyte in the same manner as in Example 1.

Example 3

An electrolyte was prepared in the same manner as in example 1, except that when preparing the electrolyte, 0.5 mass % triallyl of isocyanurate and 0.5 mass % of diglycolic anhydride were dissolved to prepare the electrolyte. A cylindrical battery was produced using the electrolyte in the same manner as in Example 1.

Example 4

An electrolyte was prepared in the same manner as in Example 1, except that when preparing the electrolyte, 0.5 mass % of triallyl isocyanurate and 0.75 mass % of diglycolic anhydride were dissolved to prepare the electrolyte. A cylindrical battery was produced using the electrolyte in the same manner as in Example 1.

Example 5

An electrolyte was prepared in the same manner as in Example 1, except that when preparing the electrolyte, 0.5 mass % of triallyl isocyanurate and 1.5 mass % of diglycolic anhydride were dissolved to prepare the electrolyte. A cylindrical battery was produced using the electrolyte in the same manner as in Example 1.

Example 6

An electrolyte was prepared in the same manner as in Example 1, except that when preparing the electrolyte, 0.25 mass % of triallyl isocyanurate and 0.5 mass % of diglycolic anhydride were dissolved to prepare the electrolyte. A cylindrical battery was produced using the electrolyte in the same manner as in Example 1.

Example 7

An electrolyte was prepared in the same manner as in Example 1, except that when preparing the electrolyte, 1.0 mass % of triallyl isocyanurate and 0.5 mass % of diglycolic anhydride were dissolved to prepare the electrolyte. A cylindrical battery was produced using the electrolyte in the same manner as in Example 1.

Example 8

An electrolyte was prepared in the same manner as in Example 1, except that when preparing the electrolyte, 1.5 mass % of triallyl isocyanurate and 0.5 mass % of diglycolic anhydride were dissolved to prepare the electrolyte. A cylindrical battery was produced using the electrolyte in the same manner as in Example 1.

Example 9

An electrolyte was prepared in the same manner as in Example 1, except that when preparing the electrolyte, 0.5 mass % of diallyl isocyanurate and 0.5 mass % of diglycolic anhydride were dissolved to prepare the electrolyte. A cylindrical battery was produced using the electrolyte in the same manner as in Example 1. Diallyl isocyanurate is represented by the formula below.

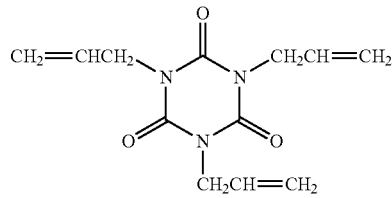

[Formula 6]

Comparative Example 1

An electrolyte was prepared in the same manner as in Example 1, except that when preparing the electrolyte, triallyl isocyanurate or diglycolic anhydride was not added. A cylindrical battery was produced using the electrolyte in the same manner as in Example 1.

Comparative Example 2

An electrolyte was prepared in the same manner as in Example 1, except that when preparing the electrolyte, diglycolic anhydride was not added. A cylindrical battery was produced using the electrolyte in the same manner as in Example 1.

Comparative Example 3

An electrolyte was prepared in the same manner as in Example 9, except that when preparing the electrolyte, diallyl isocyanurate or diglycolic anhydride was not added. A cylindrical battery was produced using the electrolyte in the same manner as in Example 9.

Comparative Example 4

An electrolyte was prepared in the same manner as in Example 9, except that when preparing the electrolyte, diglycolic anhydride was not added. A cylindrical battery was produced using the electrolyte in the same manner as in Example 1.

[Charging/Discharging Test]

A single charging/discharging cycle was carried out on each of batteries of Example 1 and Comparative Examples 1 and 2 under conditions of a temperature of 25° C., a charging/discharging current corresponding to 0.5 It, a charge cutoff voltage of 4.1 V, and a discharge cutoff voltage of 3.0 V. The difference in the discharge capacity between each of batteries according to Example 1 and Comparative Examples 1 and 2 and that according to Comparative Example 1 as the reference was calculated. The results are shown in Table 1.

A single charging/discharging cycle was carried out on each of batteries of Example 9 and Comparative Examples 3 and 4 under conditions of a temperature of 25° C., a charging/discharging current corresponding to 0.25 It, a charge cutoff voltage of 4.1 V, and a discharge cutoff voltage of 3.0 V. The difference in the discharge capacity between each of batteries according to Example 9 and Comparative Examples 3 and 4 and that according to Comparative Example 3 as the reference was calculated. The results are shown in Table 2.

[Cycle Test at High Temperature]

100 charging/discharging cycles were carried out on each of batteries of Example 1 and Comparative Examples 1 and 2 in an environment at a high temperature of 45° C. under conditions of a charging/discharging current corresponding to 0.5 lt, a charge cutoff voltage of 4.1 V, and a discharge cutoff voltage of 3.0 V. The discharge capacity loss after 100 cycles was calculated (the discharge capacity at the first cycle–the discharge capacity at the 100th cycle). The results are shown in Table 1.

100 charging/discharging cycles were carried out on each of batteries of Example 9 and Comparative Examples 3 and 4 in an environment at a high temperature of 45° C. under conditions of a charging/discharging current corresponding to 0.25 lt, a charge cutoff voltage of 4.1 V, and a discharge cutoff voltage of 3.0 V. The discharge capacity loss after 100 cycles was calculated (the discharge capacity at the first cycle–the discharge capacity at the 100th cycle). The results are shown in Table 1.

TABLE 1

| | Additive 1 (mass %) | Additive 2 (mass %) | Difference in initial capacity from Comparative Example 1 as reference | Capacity loss after 100 cycles |
|---|---|---|---|---|
| Example 1 | Diglycolic anhydride (0.5) | Triallyl isocyanurate (0.75) | 40 mAh | −120 mAh |
| Comparative Example 1 | — | — | 0 mAh | −188 mAh |
| Comparative Example 2 | — | Triallyl isocyanurate (0.75) | −8 mAh | −174 mAh |

TABLE 2

| | Additive 1 (mass %) | Additive 2 (mass %) | Difference in initial capacity from Comparative Example 1 as reference | Capacity loss after 100 cycles |
|---|---|---|---|---|
| Example 9 | Diglycolic anhydride (0.5) | Diallyl isocyanurate (0.5) | 21 mAh | −194 mAh |
| Comparative Example 3 | — | — | 0 mAh | −201 mAh |
| Comparative Example 4 | — | Diallyl isocyanurate (0.5) | 8 mAh | −196 mAh |

[Storage Stability Test at High Temperature]

A single charging/discharging cycle was carried out on each of batteries of Examples 2 to 8 under conditions of a temperature of 25° C., a charging/discharging current corresponding to 0.5 lt, a charge cutoff voltage of 4.1 V, and a discharge cutoff voltage of 3.0 V, and then charging was carried out thereon to a charge cutoff voltage of 4.1 V. The charged batteries were stored in an environment at a high temperature of 40° C. for 7 days. Each of the batteries after storage was once discharged to 3.0 V, charged to 4.1 V again, and then discharged to 3.0 V, at a charging/discharging current corresponding to 0.5 lt under the condition of a temperature of 25° C. The discharge capacity at this time is shown in Table 3 and Table 4 in terms of a percentage based on the discharge capacity of the battery before the storage, which represents the capacity retention rate after storage at 40° C. for 7 days.

TABLE 3

| | Additive 1 (mass %) | Additive 2 (mass %) | Capacity retention rate after storage at 40° C. for 7 days |
|---|---|---|---|
| Example 2 | Diglycolic anhydride (0.25) | Triallyl isocyanurate (0.5) | 96% |
| Example 3 | Diglycolic anhydride (0.5) | Triallyl isocyanurate (0.5) | 98% |
| Example 4 | Diglycolic anhydride (0.75) | Triallyl isocyanurate (0.5) | 96% |
| Example 5 | Diglycolic anhydride (1.5) | Triallyl isocyanurate (0.5) | 89% |

TABLE 4

| | Additive 1 (mass %) | Additive 2 (mass %) | Capacity retention rate after storage at 40° C. for 7 days |
|---|---|---|---|
| Example 6 | Diglycolic anhydride (0.5) | Triallyl isocyanurate (0.25) | 99% |
| Example 3 | Diglycolic anhydride (0.5) | Triallyl isocyanurate (0.5) | 98% |
| Example 7 | Diglycolic anhydride (0.5) | Triallyl isocyanurate (0.75) | 93% |
| Example 8 | Diglycolic anhydride (0.5) | Triallyl isocyanurate (1.5) | 90% |

Each battery of Examples provided an increased initial discharge capacity and also a small decrease in the capacity due to charging/discharging cycles in an environment at a high temperature, compared to the batteries of Comparative Examples. It can be said from these results that the addition of both the isocyanuric acid derivative and the cyclic carboxylic anhydride can prevent the decrease in the capacity due to charging/discharging cycles in an environment at a high temperature and also improve the initial capacity even in a non-aqueous electrolyte secondary battery in which a positive electrode active material including a Ni-containing lithium composite oxide as a main component is used. In addition, when the content of the isocyanuric acid derivative and that of the cyclic carboxylic anhydride are both within the range of 1.5 mass % or less, a large decrease in the capacity can be prevented also in the storage stability test at a high temperature.

The invention claimed is:

1. A non-aqueous electrolyte secondary battery comprising:
   a positive electrode including a positive electrode active material that comprises a Ni-containing lithium composite oxide as a main component;
   a negative electrode; and
   a non-aqueous electrolyte;
   wherein the non-aqueous electrolyte includes:
   a non-aqueous solvent including a fluorine-containing cyclic carbonate;
   an isocyanuric acid derivative represented by the formula below:

[Formula 1]

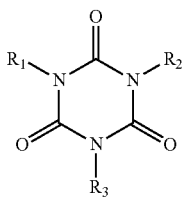

wherein $R_1$ to $R_3$ are each independently $-C_nH_{2n}-CH=CH_2$ or hydrogen, provided that at least one of $R_1$ to $R_3$ is $-C_nH_{2n}-CH=CH_2$; and n is an integer; and a cyclic carboxylic anhydride represented by the formula below:

[Formula 2]

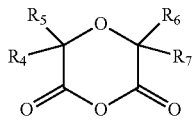

wherein $R_4$ to $R_7$ are each independently hydrogen, an alkyl group, an alkene group, or an aryl group.

2. The non-aqueous electrolyte secondary battery according to claim 1, wherein the content of the fluorine-containing cyclic carbonate is 0.1 vol % or more and 30 vol % or less based on the total volume of the non-aqueous solvent.

3. The non-aqueous electrolyte secondary battery according to claim 1, wherein the content of the cyclic carboxylic anhydride is 0.1 mass % or more and 1.5 mass % or less based on the total mass of the non-aqueous electrolyte.

4. The non-aqueous electrolyte secondary battery according to claim 1, wherein the content of the isocyanuric acid derivative is 0.1 mass % or more and 1.5 mass % or less based on the total mass of the non-aqueous electrolyte.

5. The non-aqueous electrolyte secondary battery according to claim 1, wherein the cyclic carboxylic anhydride includes diglycolic anhydride.

6. The non-aqueous electrolyte secondary battery according to claim 1, wherein the isocyanuric acid derivative includes triallyl isocyanurate.

* * * * *